(12) United States Patent
Sinnett et al.

(10) Patent No.: US 6,183,963 B1
(45) Date of Patent: Feb. 6, 2001

(54) DETECTION OF CYP1A1, CYP3A4, CYP2D6 AND NAT2 VARIANTS BY PCR-ALLELE-SPECIFIC OLIGONUCLEOTIDE (ASO) ASSAY

(75) Inventors: Daniel Sinnett, Boucherville; Damian Labuda, Montréal, both of (CA)

(73) Assignee: Signalgene, Montreal (CA)

( * ) Notice: Under 35 U.S.C. 154(b), the term of this patent shall be extended for 0 days.

(21) Appl. No.: 09/177,359

(22) Filed: Oct. 23, 1998

(51) Int. Cl.[7] .............................. C12Q 1/68; C12P 19/34; G01N 33/566; C07H 21/04
(52) U.S. Cl. ...................... 435/6; 435/91.2; 435/803; 436/501; 536/24.31; 536/24.33
(58) Field of Search ................. 435/6, 91.2, 803; 436/501; 536/24.31, 24.33

(56) References Cited

U.S. PATENT DOCUMENTS 4,966,837 * 10/1990 Brown et al. ............................ 435/6
5,527,677 * 6/1996 Deguchi et al. ......................... 435/6

OTHER PUBLICATIONS

Iwabuchi et al., "Biochemical and Genetic Characterization of 2–Carboxybenzaldehyde Dehydrogenase, an enzyme involved in Phenanthrene degradation by Nocardiodies sp. strain KP7", Journal of Bacteriology, vol. 179 (20), pp. 6488–6494, Oct. 1997.*

Hashimoto et al., "Gene structure of CYP3A4, an adult–specific form of cytochrome P450 in human livers, and its transcriptional control", European Journal of Biochemistry, vol. 218 (2), pp. 585–595, 1993.*

Cascorbi I et al. 1996a, *Cancer Res* 56:3961–3966.
Cascorbi I, Brockmöller J, Roots, 1996b, *Cancer Res* 56:4965–4969.
Hashimoto H et al., 1993, *Eur J Biochem.* 218:585–595.
Sachse C et al., 1997, *Am J Hum Genet* 60:28.
Shields PG et al., 1993, *Cancer Res.* 53:3486–3492.
Taioli E et al., 1995, *Toxicol Let* 77:357.

* cited by examiner

*Primary Examiner*—Jeffrey Fredman
*Assistant Examiner*—Arun Chakrabarti
(74) *Attorney, Agent, or Firm*—Swabey Ogilvy Renault; France Côté

(57) ABSTRACT

The present invention relates to a method of detecting genetic variation in individuals by PCR amplification of the locus of interest, transferring the resulting PCR products to a membrane filter, hybridizing with allele-specific-oligonucleotides (ASOs), and visualizing the results. Such a method is in the field of diagnostics, pharmacogenetics, cancer therapeutics, and drug metabolism. In particular, the present invention relates to the detection of genetic polymorphisms in gene encoding xenobiotics metabolizing enzymes CYP1A1, CYP2D6, CYP3A4, and NAT2.

18 Claims, 6 Drawing Sheets

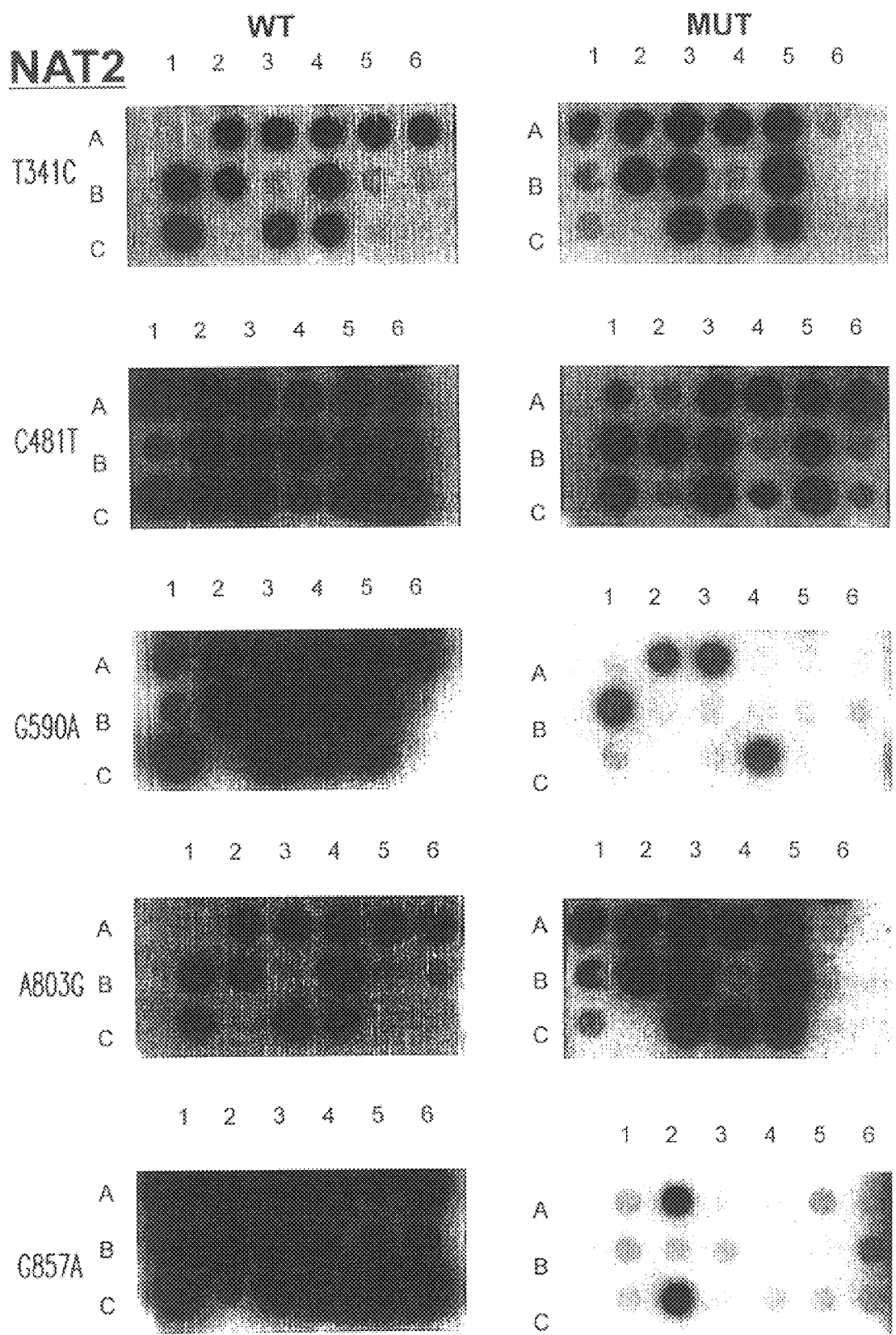

US 6,183,963 B1

SEQUENCE LISTING

<160> NUMBER OF SEQ ID NOS: 37

<210> SEQ ID NO 1
<211> LENGTH: 22
<212> TYPE: DNA
<213> ORGANISM: Artificial Sequence
<220> FEATURE:
<223> OTHER INFORMATION: cDNA for use as primers

<400> SEQUENCE: 1
gtcacacgag gaaatcaaat gc                    22

```
<210> SEQ ID NO 2
<211> LENGTH: 32
<212> TYPE: DNA
<213> ORGANISM: Artificial Sequence
<220> FEATURE:
<223> OTHER INFORMATION: cDNA for use as primers

<400> SEQUENCE: 2
acccagcatc gacaatgtaa ttcctgccct ca                                    32

<210> SEQ ID NO 3
<211> LENGTH: 24
<212> TYPE: DNA
<213> ORGANISM: Artificial Sequence
<220> FEATURE:
<223> OTHER INFORMATION: cDNA for use as primers

<400> SEQUENCE: 3
gttttctagc atgaatcact ctgc                                             24

<210> SEQ ID NO 4
<211> LENGTH: 20
<212> TYPE: DNA
<213> ORGANISM: Artificial Sequence
<220> FEATURE:
<223> OTHER INFORMATION: cDNA for use as primers

<400> SEQUENCE: 4
cctggaccaa atcaggagag                                                  20

<210> SEQ ID NO 5
<211> LENGTH: 22
<212> TYPE: DNA
<213> ORGANISM: Artificial Sequence
<220> FEATURE:
<223> OTHER INFORMATION: cDNA for use as primers

<400> SEQUENCE: 5
acacaagggt ttattttgtt cc                                               22

<210> SEQ ID NO 6
<211> LENGTH: 20
<212> TYPE: DNA
<213> ORGANISM: Artificial Sequence
<220> FEATURE:
<223> OTHER INFORMATION: cDNA for use as primers

<400> SEQUENCE: 6
ggctgagcaa tctgaccctg                                                  20

<210> SEQ ID NO 7
<211> LENGTH: 21
<212> TYPE: DNA
<213> ORGANISM: Artificial Sequence
<220> FEATURE:
<223> OTHER INFORMATION: cDNA for use as primers

<400> SEQUENCE: 7
taggagtctt gtctcatgcc t                                                21

<210> SEQ ID NO 8
<211> LENGTH: 25
<212> TYPE: DNA
<213> ORGANISM: Artificial Sequence
<220> FEATURE:
<223> OTHER INFORMATION: cDNA for use as primers
```

<400> SEQUENCE: 8
ctgtctccct ctggttacag gaagc                                    25

<210> SEQ ID NO 9
<211> LENGTH: 25
<212> TYPE: DNA
<213> ORGANISM: Artificial Sequence
<220> FEATURE:
<223> OTHER INFORMATION: cDNA for use as primers

<400> SEQUENCE: 9
ttccacccgt tgcagcagga tagcc                                    25

<210> SEQ ID NO 10
<211> LENGTH: 19
<212> TYPE: DNA
<213> ORGANISM: Artificial Sequence
<220> FEATURE:
<223> OTHER INFORMATION: cDNA for use as primers

<400> SEQUENCE: 10
gccttcgcca accactccg                                           19

<210> SEQ ID NO 11
<211> LENGTH: 20
<212> TYPE: DNA
<213> ORGANISM: Artificial Sequence
<220> FEATURE:
<223> OTHER INFORMATION: cDNA for use as primers

<400> SEQUENCE: 11
aaatcctgct cttccgaggc                                          20

<210> SEQ ID NO 12
<211> LENGTH: 21
<212> TYPE: DNA
<213> ORGANISM: Artificial Sequence
<220> FEATURE:
<223> OTHER INFORMATION: cDNA for use as primers

<400> SEQUENCE: 12
gatgagctgc taactgagcc c                                        21

<210> SEQ ID NO 13
<211> LENGTH: 19
<212> TYPE: DNA
<213> ORGANISM: Artificial Sequence
<220> FEATURE:
<223> OTHER INFORMATION: cDNA for use as primers

<400> SEQUENCE: 13
ccgagagcat actcgggac                                           19

<210> SEQ ID NO 14
<211> LENGTH: 21
<212> TYPE: DNA
<213> ORGANISM: Artificial Sequence
<220> FEATURE:
<223> OTHER INFORMATION: cDNA for use as primers

<400> SEQUENCE: 14
taggtaaaga tctgtaggtg t                                        21

<210> SEQ ID NO 15
<211> LENGTH: 18

```
<212> TYPE: DNA
<213> ORGANISM: Artificial Sequence
<220> FEATURE:
<223> OTHER INFORMATION: cDNA for use as primers

<400> SEQUENCE: 15
gcttctccac cttggaag                                                    18

<210> SEQ ID NO 16
<211> LENGTH: 15
<212> TYPE: DNA
<213> ORGANISM: Artificial Sequence
<220> FEATURE:
<223> OTHER INFORMATION: cDNA for use as probes

<400> SEQUENCE: 16
ggtgaccact gacgg                                                       15

<210> SEQ ID NO 17
<211> LENGTH: 15
<212> TYPE: DNA
<213> ORGANISM: Artificial Sequence
<220> FEATURE:
<223> OTHER INFORMATION: cDNA for use as probes

<400> SEQUENCE: 17
ccgtcaatgg tcacc                                                       15

<210> SEQ ID NO 18
<211> LENGTH: 15
<212> TYPE: DNA
<213> ORGANISM: Artificial Sequence
<220> FEATURE:
<223> OTHER INFORMATION: cDNA for use as probes

<400> SEQUENCE: 18
atttggtcca agtac                                                       15

<210> SEQ ID NO 19
<211> LENGTH: 15
<212> TYPE: DNA
<213> ORGANISM: Artificial Sequence
<220> FEATURE:
<223> OTHER INFORMATION: cDNA for use as probes

<400> SEQUENCE: 19
gtacctggac caaat                                                       15

<210> SEQ ID NO 20
<211> LENGTH: 15
<212> TYPE: DNA
<213> ORGANISM: Artificial Sequence
<220> FEATURE:
<223> OTHER INFORMATION: cDNA for use as probes

<400> SEQUENCE: 20
acctcaaaca attga                                                       15

<210> SEQ ID NO 21
<211> LENGTH: 15
<212> TYPE: DNA
<213> ORGANISM: Artificial Sequence
<220> FEATURE:
<223> OTHER INFORMATION: cDNA for use as probes

<400> SEQUENCE: 21
```

-continued

```
tcaattgttc gaggt                                                    15

<210> SEQ ID NO 22
<211> LENGTH: 15
<212> TYPE: DNA
<213> ORGANISM: Artificial Sequence
<220> FEATURE:
<223> OTHER INFORMATION: cDNA for use as probes

<400> SEQUENCE: 22
agtgctgaaa aatat                                                    15

<210> SEQ ID NO 23
<211> LENGTH: 15
<212> TYPE: DNA
<213> ORGANISM: Artificial Sequence
<220> FEATURE:
<223> OTHER INFORMATION: cDNA for use as probes

<400> SEQUENCE: 23
atatttctca gcact                                                    15

<210> SEQ ID NO 24
<211> LENGTH: 15
<212> TYPE: DNA
<213> ORGANISM: Artificial Sequence
<220> FEATURE:
<223> OTHER INFORMATION: cDNA for use as probes

<400> SEQUENCE: 24
cctggtgatg aatcc                                                    15

<210> SEQ ID NO 25
<211> LENGTH: 15
<212> TYPE: DNA
<213> ORGANISM: Artificial Sequence
<220> FEATURE:
<223> OTHER INFORMATION: cDNA for use as probes

<400> SEQUENCE: 25
ggatccatca ccagg                                                    15

<210> SEQ ID NO 26
<211> LENGTH: 15
<212> TYPE: DNA
<213> ORGANISM: Artificial Sequence
<220> FEATURE:
<223> OTHER INFORMATION: cDNA for use as probes

<400> SEQUENCE: 26
tgagcccagg aggtg                                                    15

<210> SEQ ID NO 27
<211> LENGTH: 15
<212> TYPE: DNA
<213> ORGANISM: Artificial Sequence
<220> FEATURE:
<223> OTHER INFORMATION: cDNA for use as probes

<400> SEQUENCE: 27
cacctcccgg gctca                                                    15

<210> SEQ ID NO 28
<211> LENGTH: 15
<212> TYPE: DNA
<213> ORGANISM: Artificial Sequence
```

```
<220> FEATURE:
<223> OTHER INFORMATION: cDNA for use as probes

<400> SEQUENCE: 28
gggcaacggt ctcac                                                          15

<210> SEQ ID NO 29
<211> LENGTH: 15
<212> TYPE: DNA
<213> ORGANISM: Artificial Sequence
<220> FEATURE:
<223> OTHER INFORMATION: cDNA for use as probes

<400> SEQUENCE: 29
gtgagaccat tgccc                                                          15

<210> SEQ ID NO 30
<211> LENGTH: 15
<212> TYPE: DNA
<213> ORGANISM: Artificial Sequence
<220> FEATURE:
<223> OTHER INFORMATION: cDNA for use as probes

<400> SEQUENCE: 30
gtgagaccat tgccc                                                          15

<210> SEQ ID NO 31
<211> LENGTH: 15
<212> TYPE: DNA
<213> ORGANISM: Artificial Sequence
<220> FEATURE:
<223> OTHER INFORMATION: cDNA for use as probes

<400> SEQUENCE: 31
gtgagaacat tgccc                                                          15

<210> SEQ ID NO 32
<211> LENGTH: 10
<212> TYPE: DNA
<213> ORGANISM: Artificial Sequence
<220> FEATURE:
<223> OTHER INFORMATION: cDNA for use as probes

<400> SEQUENCE: 32
ggcgtcctgg                                                                10

<210> SEQ ID NO 33
<211> LENGTH: 9
<212> TYPE: DNA
<213> ORGANISM: Artificial Sequence
<220> FEATURE:
<223> OTHER INFORMATION: cDNA for use as probes

<400> SEQUENCE: 33 ggcgtctgg                                                                  9

<210> SEQ ID NO 34
<211> LENGTH: 15
<212> TYPE: DNA
<213> ORGANISM: Artificial Sequence
<220> FEATURE:
<223> OTHER INFORMATION: cDNA for use as probes

<400> SEQUENCE: 34
gagcacagga tgacc                                                          15
```

-continued

```
<210> SEQ ID NO 35
<211> LENGTH: 15
<212> TYPE: DNA
<213> ORGANISM: Artificial Sequence
<220> FEATURE:
<223> OTHER INFORMATION: cDNA for use as probes

<400> SEQUENCE: 35
tgagcacgga tgacc                                                        15

<210> SEQ ID NO 36
<211> LENGTH: 19
<212> TYPE: DNA
<213> ORGANISM: Artificial Sequence
<220> FEATURE:
<223> OTHER INFORMATION: cDNA for use as probes

<400> SEQUENCE: 36
agagacaagg gcaagagag                                                    19

<210> SEQ ID NO 37
<211> LENGTH: 19
<212> TYPE: DNA
<213> ORGANISM: Artificial Sequence
<220> FEATURE:
<223> OTHER INFORMATION: cDNA for use as probes

<400> SEQUENCE: 37
agagacaagg gcaggagag                                                    19
```

DETECTION OF CYP1A1, CYP3A4, CYP2D6 AND NAT2 VARIANTS BY PCR-ALLELE-SPECIFIC OLIGONUCLEOTIDE (ASO) ASSAY

BACKGROUND OF THE INVENTION (a) Field of the Invention

This invention relates to a method of detecting genetic variation in individuals by PCR amplification of the locus of interest, transferring the resulting PCR products to a membrane filter, hybridizing with allele-specific-oligonucleotides (ASOs), and visualizing the results. Such a method is in the field of diagnostics, pharmacogenetics, cancer therapeutics, and drug metabolism. In particular, the present invention relates to the detection of genetic polymorphisms in gene encoding xenobiotics metabolizing enzymes CYP1A1, CYP2D6, CYP3A4, and NAT2.

(b) Description of Prior Art

It is recognized that marked interindividual differences exist in enzymes that metabolize xenobiotics and that this variability can be genetically determined. Considerable progress has been made in identifying a number of individual enzymes that are subject to genetic polymorphism. A polymorphism is generally considered to be a stably inherited trait. Genetic variation means differences between individuals in regard to the base sequence of their DNA. Genotyping involves identification of (defined) genetic mutations that, in a particular case, give rise to the specific drug metabolism phenotypes. These mutations include genetic alterations that lead to increased activity, absence of an active protein (null allele) or production of a mutant protein with altered catalytic capacity. A number of types of genetic polymorphism in xenobiotics metabolizing enzymes are relevant to clinical practice. These include those relating to N-ace-tyltransferase 2 (NAT2) and the cytochromes P450 1A1 (CYP1A1), 3A4 (CYP3A4) and 2D6 (CYP2D6). Genetic variation can be detected by means of electrophoresis of DNA fragments, generated by digestion of PCR products with a restriction enzyme the so-called PCR-RFLP approach. This method that has proven useful in screening for genetic mutations associated with altered metabolism of drugs and/or cancer susceptibility. It consists of amplification of a specific region of the gene of interest by PCR followed by digestion of the amplified DNA product with restriction endonucleases. Restriction endonucleases have the capacity to digest DNA with a high degree of nucleotide sequence specificity. Thus, point mutations within the recognition sequence of a specific restriction endonuclease may be detected through determining whether the DNA of interest serves as a substrate for that endonuclease. These studies are routinely carried out by comparing the size of digestion products generated from a DNA substrate amplified from control subject DNA with respect to study subject DNAS. The size of the digestion products is easily evaluated by agarose gel electrophoresis with ethidium bromide staining and UV transillumination. In this case the position of the bands varies between individuals, as a result of gain or loss of the recognition site for the restriction enzyme used, this is restriction fragment length polymorphism (RFLP). However, the PCR-RFLP is not well suited for genotyping a considerable number of samples that are usually analyzed in such investigations.

It would be highly desirable to be provided with a PCR-based assay to detect point mutations in CYP1A1, CYP2D6, CYP3A4 and NAT2.

SUMMARY OF THE INVENTION

The present invention relates to the development of a PCR-based assay to detect point mutations in CYP1A1, CYP2D6, CYP3A4 and NAT2. The presence of these mutant alleles is associated with an altered enzyme activity potentially leading (i) to toxicity when individuals are treated with standard doses of certain prescribed drugs or (ii) to increased susceptibility to cancer following environmental exposures. Detection of DNA common variants at the CYP1A1, CYP2D6, CYP3A4 and NAT2 loci would offer a strategy for identifying individuals <<at risk>> based on their genotype, prior to treatment with potentially toxic doses of drugs or to exposure to environmental toxins. Another approach for detection of specific mutations within a gene of interest is through hybridization of the PCR products with allele-specific oligonucleotide (ASO) probes for the wild type or variant alleles utilized in parallel hybridizations. Only the oligonucleotide that precisely hybridizes to the target sequences produces a signal from a labeled probe. This genotyping method, which require small amounts of nucleated cells derived from a variety of sources, is not affected by the underlying disease or by drugs taken by the patient. It provides results within 24–48 h, allowing for rapid intervention.

One aim of the present invention is to provide a diagnostic test to identify individuals with altered xenobiotics-metabolizing activities based on their genotypes. Such diagnostic test to determine genotype of individuals is quite advantageous because measuring the enzymatic activity has many limitations. To achieve this goal, 11 different tests, 3 to detect mutations in CYP1A1 alleles, 2 for CYP2D6, 1 for CYP3A4 and 5 for NAT2 variants, have been developed. These tests involved PCR-based amplification of these genes where the mutations of interest are found. Following amplification, the amplified fragments are dot blotted on a membrane filter and assayed for the presence or absence of the specific mutation of interest (i.e. at least one of the 11 mutations). Although much of these assays can be done in any molecular biology facilities, procedures and kits are designed that contain all the reagents, primers and solutions for the genotyping test to facilitate the procedure for use in general clinical laboratories, such as those found in a typical hospital, clinic and even private reference laboratories.

In accordance with the present invention there is provided an isolated oligonucleotide molecule comprising a mutant allele of CYP1A1, which contains a point mutation at one position selected from the group consisting of position 4887, 4889, and 6235, such as an adenine at position 4887, a guanine at position 4889 and a cytosine at position 6235. The mutant oligonucleotide molecules have a nucleic acid sequence as set forth in SEQ ID NOS:27, 28 and 31.

1. In accordance with the present invention there is provided an isolated oligonucleotide molecule comprising a wild-type allele of CYP1A1, which contains a normal nucleotide at one position selected from the group consisting of position 4887, 4889, and 6235, such as a cytosine at position 4887, a adenine at position 4889 and a thymine at position 6235. The wild type oligonucleotide molecules have a nucleic acid sequence as set forth in SEQ ID NOS:26, 29 and 30.

In accordance with the present invention there is provided an isolated oligonucleotide molecule comprising a mutant allele of CYP3A4, which contains a point mutation at position −290, such as a guanine. The mutant oligonucleotide molecule has a nucleic acid sequence as set forth in SEQ ID NO:37.

In accordance with the present invention there is provided an isolated oligonucleotide molecule comprising a wild-type allele of CYP3A4, which contains a normal nucleotide at position 290, such as an adenine. The wild type oligonucleotide molecule have a nucleic acid sequence as set forth in SEQ ID NO:36.

In accordance with the present invention there is provided an isolated oligonucleotide molecule comprising a mutant allele of CYP2D6, which contains a point mutation at one position selected from the group consisting of position 1934 and 2637, such as an adenine at position 1934 and a deletion at position 2637. The mutant oligonucleotide molecules have a nucleic acid sequence as set forth in SEQ ID NOS:33 and 35.

In accordance with the present invention there is provided an isolated oligonucleotide molecule comprising a wild-type allele of CYP2D6, which contains a normal nucleotide at one position selected from the group consisting of position 1934 and 2637, such as a guanine at position 1934 and an adenine at position 2637. The wild type oligonucleotide molecules have a nucleic acid sequence as set forth in SEQ ID NOS:32 and 34.

In accordance with the present invention there is provided an isolated oligonucleotide molecule comprising a mutant allele of NAT2, which is at least 11 consecutive bases long and contains a point mutation at one position selected from the group consisting of position 341, 481, 590, 803, and 857, such as a cytosine at position 341, a thymine at position 481, an adenine at position 590, a guanine at position 803, and an adenine at position 857.

The mutant oligonucleotide molecules have a nucleic acid sequence as set forth in SEQ ID NOS:16, 18, 20, 23, and 24.

In accordance with the present invention there is provided an isolated oligonucleotide molecule comprising a wild-type allele of NAT2, which contains a normal nucleotide at one position selected from the group consisting of position 341, 481, 590, 803, and 857, such as a thymine at position 341, a cytosine at position 481, a guanine at position 590, an adenine at position 803, and a guanine at position 857. The wild type oligonucleotide molecules have a nucleic acid sequence as set forth in SEQ ID NOS:17, 19, 21, 22, and 25.

In accordance with the present invention there is provided an oligonucleotide molecule complementary to any of the oligonucleotide molecules identified as SEQ ID NOS:16–37.

In accordance with the present invention there is provided a diagnostic assay for determining DNA variants in CYP1A1, CYP3A4, CYP2D6 or NAT2 gene in a subject, which comprises the steps of:
  a) obtaining a genomic DNA sample of said subject;
  b) amplifying the DNA sample of step a) using primers which are flanking the polymorphic site of at least one of CYP1A1, CYP3A4, CYP2D6 and NAT2 genes;
  c) subjecting the amplified fragment of step b) to Southern dot blot transfer on membrane; and hybridizing the dot-blots obtained in (c) in parallel with allele-specific oligonucleotides (ASO) probes corresponding to wild type and variant alleles to determine CYP1A1, CYP3A4, CYP2D6 or NAT2 genotype of said subject.

In accordance with a preferred embodiment of the present invention, the amplifying step b) is effected with PCR primers set forth in Table 1.

In accordance with a preferred embodiment of the present invention, a labeled ASO probe is used in step d) and is selected from the sequences set forth in Table 2 and hybridizes under stringent conditions (Table 2).

In accordance with the present invention there is provided a diagnostic kit for determining DNA variants in CYP1A1, CYP3A4, CYP2D6 or NAT2 gene in a subject, which comprises:
  a) PCR primers set forth in SEQ ID NOS:1–15; and
  b) ASO probes set forth in SEQ ID NOS:16–37.

BRIEF DESCRIPTION OF THE DRAWINGS

FIGS. 5A to 5C illustrate representative results of the PCR-ASO hybridizations of mutations in the CYP1A1, CYP2D6, CYP3A4 and NAT2 loci.

DETAILED DESCRIPTION OF THE INVENTION

Figure 1:
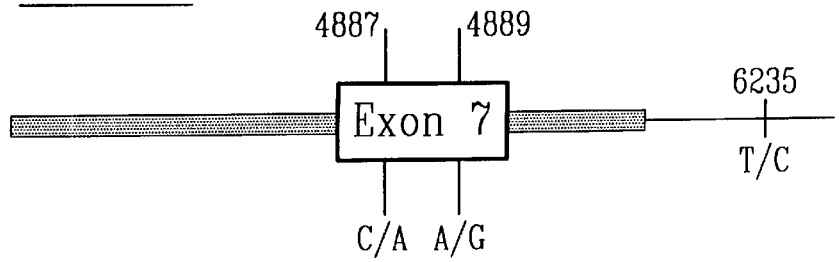
FIG. 1 illustrates mutations in the CYP1A1locus.

A large number of enzymes exist to metabolize xenobiotics including drugs and environmental pollutants. Most of them have been classified as belonging to phase I or phase II pathways of metabolism. Virtually all chemicals ingested or absorbed by the body will be metabolized to some degree. Phase I enzymes include reductases, oxidases and hydrolases, while the phase II enzymes are all transferases. These reactions serve to transform a hydrophobic compound into a form that is more water soluble and can be easily eliminated from the organism through urine or bile. Polymorphism in xenobiotics metabolizing enzymes can be associated with marked differences in response to drug therapy and/or may also cause increased susceptibility to environmentally based diseases such as cancer. Differences in metabolism of therapeutics can lead to severe toxicity or therapeutic failure by altering the relation between dose and blood concentration of the pharmacologically active drug. The variability in metabolizing capacity is due to the presence of mutant alleles for which the differences in DNA sequence from the wild-type allele have been established, the prerequisite for the development of a PCR-based test for genotyping. Thus, in pharmacogenetic studies one applies genotyping of polymorphic alleles encoding drug-metabolizing enzymes to the identification of an individual's drug metabolism phenotype. A unique combination of polymorphism in 2 or more of these enzymes might render an individual susceptible to diseases such as cancer or neurotoxicity. Determination of these genetic polymorphism may be of clinical value in predicting adverse or inadequate response to certain therapeutic agents and in predicting increased risk of environmental or occupational exposure-linked disease.

Individuals that possess modified abilities to metabolize carcinogens are at increased risk of cancer. This is because sporadic cancers result from mutations in transforming genes and carcinogen-detoxification influences the mutational events in these genes. Polymorphisms in genes encoding carcinogen-metabolizing enzymes may have relevance in determining susceptibility to cancer—individuals carrying the more active form of an enzyme involved in the activation of carcinogens or less efficient alleles of detoxifying enzymes, will be at greater risk of cancer. For this reason, two classes of genes have attracted interest: cytochromes P-450 and N-acetyltransferases. Genetic variants have been described in CYP1A1, CYP2D6 and NAT2 genes. Several studies have reported associations between these variants and altered risk of a variety of cancers, including those of the lung, bladder, gastro-intestinal tract, skin, cervix and breast. The prevalence of each polymorphism varies greatly among different ethnic groups, as well as within the Caucasian population.

There is a growing interest in analyzing these loci, in the context of diverse molecular epidemiology studies. To date the mainstay of the NAT and CYP mutations genotyping has been PCR amplification of the DNA region of interest, followed by RFLP analysis of each known mutation (Cascorbi I et al. 1996a, Cancer Res 56:3961–3966; Cascorbi I, Brockmöller J, Roots, 1996b, Cancer Res 56:4965–4969; Sachse C et al., 1997, Am J Hum Genet 60:28; Shields PG et al., 1993, Cancer Res. 53:3486–3492; Taioli E et al., 1995, Toxicol Let 77:357 Sachse et al. 1997, Shields et al 1993, Taioli et al. 1995). To increase the efficiency and facilitate processing of the large number of samples we developed a combined approach including PCR dot blot and allele-specific oligonucleotide (ASO) hybridization. The assays involve pairs of PCR primers to amplify the alleles CYP1A1*2A, *2B and *4, the alleles CYP2D6*3 and *4, the CYP3A4*2 mutant, as well as the variants NAT2*5A, *5B, *5C, *6A, and *7B (illustrated in FIGS. 1–3). Based on the sequence of the mutant alleles provided herein, PCR primers are constructed that are complementary to the region flanking the point mutations. A primer consists of a consecutive sequence of nucleotides complementary to any region in the allele flanking the position, which is mutated in the mutant allele. According to the method of the present invention, once an amplified fragment is obtained, we can determine whether the individual tested is homozygous or heterozygous for a given DNA variant by hybridizing the dot blotted PCR fragments with ASO probes for the mutant or the wild-type alleles in parallel.

This approach has a potential for automation through the use of the 96-well microplates and robotic workstations for high sample throughput. PCR-ASO assay appears simple, efficient and cost effective, particularly if a large number of samples are to be screened for several DNA variants.

N-acetyltransferase

N-acetyltransferase 2 (NAT2) is among the earliest discovered genetic polymorphism in xenobiotics-metabolizing enzymes. Deficiency in NAT2 is found in up to 50% of Caucasians and is responsible for toxicity associated with several drugs and susceptibility to certain types of cancer. The differences in the metabolism of these compounds distinguished phenotypically slow and fast acetylators. The slow acetylation phenotype frequency worldwide ranges from about 0.1 in the Japanese population to more than 0.9 in some Mediterranean peoples. Several mutant NAT2 alleles have been found in Caucasians and Asian individuals and these can be determined by PCR-RFLP genotyping (Blum et al. 1991; Hickman and Sim 1991; Rothman et al. 1993). Five mutations T341C, 481T, G590A, A803G and G857A account for nearly all slow acetylator alleles.

Cytochromes P450

The major route of phase I drug metabolism is oxidation by cytochrome P-450 (CYP). Most clinically used drugs are metabolized to some degree by P450s. These enzymes are also principally responsible for activation of procarcinogens and promutagens.

CYP2D6.

Debrisoquine 4-hydroxylase (CYP2D6) is the most well characterized P450 polymorphism. About 25% of prescribed drugs are metabolized by CYP2D6. The polymorphism appears to have clinical consequences in the use of cardiovascular drugs and drugs used for treatment of psychiatric disorders. Genotype has been shown to closely correlate with phenotypes. It has been argued that determination of a patient's CYP2D6 genotype should be a prerequisite for treatment with antipsychotic drugs. Several null CYP2D6 alleles have been characterized and PCR-RFLP assays have been developed for convenient genotyping (Gonzalez and Meyer 1991). The most common alleles are CYP2D6*3 (1 bp deletion at pos. A2637) and *4 (splice-site mutation G1934A), accounting for over 96% of all null alleles. Individuals homozygous for any of these null alleles, completely lacking CYP2D6 activity, will be considered phenotypically poor metabolizers (PM). There are significant interethnic differences in the prevalence of the PM phenotype of CYP2D6. For example, in North American and European Caucasian populations, the prevalence of poor metabolisers is 5–10%. In contrast, the prevalence is 1.8% in American blacks, 1.0% in Chinese, and apparently absent in the Japanese population.

CYP1A1.

Aryl hydrocarbon hydroxylase (CYP1A1) catalyses the first step in the metabolism of polycyclic aromatic hydrocarbons to carcinogens. Three CYP1A1 polymorphisms have been identified in Caucasians: transition T-to-C at position 6235 (T6235C) in the 3'-flanking region, substitution A-to-G in exon 7 (G4889A) exchanging the isoleucine 462 by valine in the heme binding region, and a C-to-A transversion at position 4887 (C4887A) substituting threonine to asparagine in codon 461. The frequency of the three polymorphisms shows racial differences.

CYP3A4.

CYP3A4 is involved in the metabolism of numerous human carcinogens, steroid hormones, and drugs. Until the present invention, no genetic variant had been reported that explains the interindividual variability in CYP3A4 enzyme activity. We have identified a variant located in the 5'-untranslated region of the CYP3A4 gene. The frequency of this variant allele was estimated to be 2% in a Caucasian Canadian control population. The phenotypic consequence of this mutation is unknown but its presence within the transcriptional regulatory element NFSE suggests a potential role as functional variant.

Mutations of CYP1A1, CYP2D6, CYP3A4 and NAT2

In particular, the present invention relates to the design and utilization of oligonucleotide molecules comprising a mutant allele of CYP1A1which contains a point mutation in at least one of the positions 4887, 4889, or 6235. The point mutation at 4887 is adenine and the whole oligonucleotide has the sequences shown in Table 2. The point mutation at 4889 is guanine and the whole oligonucleotide has the sequences shown in Table 2. The point mutation at 6235 is cytosine and the whole oligonucleotide has the sequences shown in Table 2. The invention relates to the design and utilization of oligonucleotide molecules comprising a wild-type (no mutation) allele of CYP1A1 which contains the normal nucleotide in at least one of the positions 4887, 4889, or 6235. The normal residue at 4887 is cytosine and the whole oligonucleotide has the sequences shown in Table 2. The normal residue at 4889 is adenine and the whole oligonucleotide has the sequences shown in Table 2. The normal residue at 6235 is thymine and the whole oligonucleotide has the sequences shown in Table 2.

TABLE 1

PCR primers for amplification of CYP1A1, CYP2D6, CYP3A4 and NAT2 mutant alleles

| Locus | Mutation | PCR primer | SEQ ID NO: | Product Size |
|---|---|---|---|---|
| NAT2 | T341C | P100, GTCACACGAGGAAATCAAATGC | SEQ ID NO:1 | 442 bp |
| | | R1, ACCCAGCATCGACAATGTAATTCCTGCCCTCA | SEQ ID NO:2 | |
| | C481T | P100, GTCACACGAGGAAATCAAATGC | SEQ ID NO:1 | 1211 bp |
| | | P56, GTTTTCTAGCATGAATCACTCTGC | SEQ ID NO:3 | |
| | G590A | P87, CCTGGACCAAATCAGGAGAG | SEQ ID NO:4 | 421 bp |
| | | P90, ACACAAGGGTTTATTTTGTTCC | SEQ ID NO:5 | |
| | A803G | P87, CCTGGACCAAATCAGGAGAG | SEQ ID NO:4 | 421 bp |
| | | P90, ACACAAGGGTTTATTTTGTTCC | SEQ ID NO:5 | |
| | G857A | P100, GTCACACGAGGAAATCAAATGC | SEQ ID NO:1 | 1211 bp |
| | | P56, GTTTTCTAGCATGAATCACTCTGC | SEQ ID NO:3 | |
| CYP1A1 | T6235C | M3F, GGCTGAGCAATCTGACCCTA | SEQ ID NO:6 | 899 bp |
| | | P80, TAGGAGTCTTGTCTCATGCCT | SEQ ID NO:7 | |
| | A4889G | M2F, CTGTCTCCCTCTGGTTACAGGAAGC | SEQ ID NO:8 | 204 bp |
| | | M2R, TTCCACCCGTTGCAGCAGGATAGCC | SEQ ID NO:9 | |
| | C4887A | M2F, CTGTCTCCCTCTGGTTACAGGAAGC | SEQ ID NC:8 | 204 bp |
| | | M2R, TTCCACCCGTTGCAGCAGGATAGCC | SEQ ID NO:9 | |
| CYP2D6 | G1934A | C, GCCTTCGCCAACCACTCCG | SEQ ID NO:10 | 334 bp |
| | | D, AAATCCTGCTCTTCCGAGGC | SEQ ID NO:11 | |
| | A2637del | E, GATGAGCTGCTAACTGAGCCC | SEQ ID NO:12 | 268 bp |
| | | F, CCGAGAGCATACTCGGGAC | SEQ ID NO:13 | |
| CYP3A4 | A-290G | 3A4F2, TAGGTAAAGATCTGTAGGTGT | SEQ ID NO:14 | 266 bp |
| | | 3A4R1, GCTTCTCCACCTTGGAAG | SEQ ID NO:15 | |

In particular, the present invention relates to the design and utilization of oligonucleotide molecules comprising a mutant allele of CYP2D6 which contains a point mutation in at least one of the positions 1934, or 2637. The point mutation at 1934 is adenine and the whole oligonucleotide has the sequences shown in Table 2. The point mutation at 2637 is a deletion of an adenine and the whole oligonucleotide has the sequences shown in Table 2. The invention relates to the design and utilization of oligonucleotide molecules comprising a wild-type (no mutation) allele of CYP2D6 which contains the normal nucleotide in at least one of the positions 1934 or 2637. The normal residue at 1934 is guanine and the whole oligonucleotide has the sequences shown in Table 2. The normal residue at 2637 is adenine and the whole oligonucleotide has the sequences shown in Table 2.

TABLE 2

Characteristics of allele-specific-oligonucleotide probes

| Locus | Mutation | | ASO | SEQ ID NO: | Hyb. T (° C.) | Wash. (° C.) |
|---|---|---|---|---|---|---|
| NAT2 | T341C | Mut, | ggtgaccactgacgg | SEQ ID NO:16 | 42 | 42 |
| | | Wt, | ccgtcaAtggtcacc | SEQ ID NO:17 | 42 | 42 |
| | C481T | Mut, | atttggtccaAgtac | SEQ ID NO:18 | 38 | 38 |
| | | Wt, | gtacctggaccaaat | SEQ ID NO:19 | 38 | 38 |

TABLE 2-continued

Characteristics of allele-specific-oligonucleotide probes

| Locus | Mutation | ASO | | SEQ ID NO: | Hyb. T (° C.) | Wash. (° C.) |
|---|---|---|---|---|---|---|
| | G590A | Mut, | acctcAaacaattga | SEQ ID NO:20 | 37 | 37 |
| | | Wt, | tcaattgttCgaggt | SEQ ID NO:21 | 37 | 37 |
| | A803G | Wt, | agtgctgaAaaatat | SEQ ID NO:22 | 37 | 40 |
| | | Mut, | atatttCtcagcact | SEQ ID NO:23 | 42 | 37 |
| | G857A | Mut, | cctggtgatgAatcc | SEQ ID NO:24 | 42 | 42 |
| | | Wt, | ggatCcatcaccagg | SEQ ID NO:25 | 42 | 55 |
| CYP1A1 | T6235C | Wt, | tgagcccAggaggtg | SEQ ID NO:26 | 37 | 42 |
| | | Mut, | cacctccCgggctca | SEQ ID NO:27 | 37 | 42 |
| | A4889G | Mut, | gggcaaCggtctcac | SEQ ID NO:28 | 37 | 40 |
| | | Wt, | gtgagaccAttgccc | SEQ ID NO:29 | 35 | 48 |
| | C4887A | Wt, | gtgagaCcattgccc | SEQ ID NO:30 | 35 | 48 |
| | | Mut, | gtgagaAcattgccc | SEQ ID NC:31 | 37 | 38 |
| CYP2D6 | G1934A | Wt, | ggcgtcCtgg | SEQ ID NO:32 | 37 | 40 |
| | | Mut, | ggcgtcTgg | SEQ ID NO:33 | 37 | 40 |
| | A2637del | Wt, | gagcacaggatgacc | SEQ ID NO:34 | 37 | 46 |
| | | Mut, | tgagcac-ggatgacc | SEQ ID NO:35 | 37 | 46 |
| CYP3A4 | A-290G | Wt, | agagacaagggcaAgagag | SEQ ID NO:36 | 37 | 55 |
| | | Mut, | agagacaagggcaGgagag | SEQ ID NO:37 | 37 | 55 |

Wt, wild-type sequence; mut, mutant sequence; uppercase characters indicate point mutation sites In particular, the present invention relates to the design and utilization of oligonucleotide molecules comprising a mutant allele of CYP3A4 which contains a point mutation in the position −290. The point mutation at −290 is guanine and the whole oligonucleotide has the sequences shown in Table 2. The invention relates to the design and utilization of oligonucleotide molecules comprising a wild-type (no mutation) allele of CYP3A4 which contains the normal nucleotide in the position −290. The normal residue at −290 is adenine and the whole oligonucleotide has the sequences shown in Table 2.

In particular, the present invention relates to the design and utilization of oligonucleotide molecules comprising a mutant allele of NAT2 which contains a point mutation in at least one of the positions 341, 481, 590, 803 and 857. The point mutation at 341 is cytosine and the whole oligonucleotide has the sequences shown in Table 2. The point mutation at 481 is thymine and the whole oligonucleotide has the sequences shown in Table 2. The point mutation at 590 is adenine and the whole oligonucleotide has the sequences shown in Table 2. The point mutation at 803 is guanine and the whole oligonucleotide has the sequences shown in Table 2. The point mutation at 857 is adenine and the whole oligonucleotide has the sequences shown in Table 2. The invention relates to the design and utilization of oligonucleotide molecules comprising a wild-type (no mutation) allele of NAT2 which contains the normal nucleotide in at least one of the positions 341, 481, 590, 803 and 857. The normal residue at 341 is thymine and the whole oligonucleotide has the sequences shown in Table 2. The normal residue at 481 is cytosine and the whole oligonucleotide has the sequences shown in Table 2. The normal residue at 590 is guanine and the whole oligonucleotide has the sequences shown in Table 2. The normal residue at 803 is adenine and the whole oligonucleotide has the sequences shown in Table 2. The normal residue at 857 is guanine and the whole oligonucleotide has the sequences shown in Table 2.

Another aim of the present invention is to provide oligonucleotide molecules complementary to any of the oligonucleotide molecules described above.

Another aim of the present invention is to provide a diagnostic assay for determining CYP1A1 genotype of an individual which comprises isolating DNA from said individual; amplifying for CYP1A1 PCR fragment from said DNA, which includes at least one of the positions 4887, 4889, or 6235, thereby obtaining an amplified fragment; transferring said amplified fragments to membrane filter; hybridizing said membrane with allele-specific oligonucleotide corresponding to at least one of point mutation at the positions 4887, 4889, or 6235 and in parallel with the corresponding wild-type oligo-nucleotide; thereby determine the CYP1A1 genotype of said individual.

In a preferred embodiment of the invention, controls are run parallel to the above described reaction steps.

Another aim of the present invention is to provide a diagnostic assay for determining CYP1A1 genotype of an individual which comprises isolating DNA from said person; making a first and a second PCR primers wherein the first PCR primers is complementary to a region 5' to one of the point mutation sites at position 4887, 4889, or 6235; and the second PCR primer is complementary to a region 3' to the same one of the point mutation sites at position 4887, 4889, or 6235; amplifying the sequence in between the first and the second primers; thereby obtaining an amplified fragment. The whole sequence of the PCR primers is given in Table 1.

Another aim of the present invention is to provide a diagnostic assay for determining CYP2D6 genotype of an individual which comprises isolating DNA from said person; making a first and a second PCR primers wherein the first PCR primers is complementary to a region 5' to one of the point mutation sites at position 1934, or 2637; and the second PCR primer is complementary to a region 3' to the same one of the point mutation sites at position 1934, or 2637; amplifying the sequence in between the first and the second primers; thereby obtaining an amplified fragment. The whole sequence of the PCR primers is given in Table 1.

Another aim of the present invention is to provide a diagnostic assay for determining CYP3A4 genotype of an individual which comprises isolating DNA from said person; making a first and a second PCR primers wherein the first PCR primers is complementary to a region 5' to the point mutation site at position −290; and the second PCR primer is complementary to a region 3' to the same one of the point mutation site at position −290; amplifying the sequence in between the first and the second primers; thereby obtaining an amplified fragment. The whole sequence of the PCR primers is given in Table 1.

Another aim of the present invention is to provide a diagnostic assay for determining NAT2 genotype of an individual which comprises isolating DNA from said person; making a first and a second PCR primers wherein the first PCR primers is complementary to a region 5' to one of the point mutation sites at position 341, 481, 590, 803 or 857; and the second PCR primer is complementary to a region 3' to the same one of the point mutation sites at position 341, 481, 590, 803 or 857; amplifying the sequence in between the first and the second primers; thereby obtaining an amplified fragment. The whole sequence of the PCR primers is given in Table 1.

DNA Isolation

Genomic DNA of the individual subject is isolated by the known methods in the art, such as phenol/chloroform extraction from tissue containing nucleated cells including white blood cells, mouth epithelial cells, liver, etc.

PCR

CYP1A1 Polylmorphisms

A DNA fragment of 899 bp containing the point mutation T6235C was amplified in 20 ul containing 20 ng of genomic DNA, 0.5 uM of primers M3F (5'GGCTGAGCAATCTGACCCTA; SEQ ID NO:6) and P80 (5'TAGGAGTCTTGTCTCATGCCT; SEQ ID NO:7), 200 uM dNTPs, 10 mM Tris-HCl (pH 8.3), 2.5 mM MgCl$_2$, 50 mM KCl, and 0.5U AmpliTaq DNA polymerase (Hoffman-LaRoche). PCR was carried out for 35 cycles of 30s at 940° C., 1 min at 63° C., and min at 72° C. Mutations A4889G and C4887A were detected by amplifying a 204 bp fragment with primers M2F (5'CTGTCTCCCTCTGGTTACAGGAAGC; SEQ ID NO:8) and M2R (5'TTCCACCCGTTGCAGCAGGATAGCC; SEQ ID NO:9) as described above. These mutations were then used to define three distinct alleles (FIG. 1), CYP1A1*2A (presence of T6235C only), *2B (both T6235C and A4889G) and *4 (C4887A only).

CYP2D6 Polymorphisms

The mutant CYP2D6*4 (G-to-A transition at position 1934) and CYP2D6*3 (a 1 bp deletion in position 2637) alleles (FIG. 2) were detected by PCR amplification using primers C/D (C, 5'GCCTTCGCCAACCACTCCG (SEQ ID NO:10); D, 5'AAATCCTGCTCTTCCGAGGC; SEQ ID NO:11), and primers E/F (E, 5'GATGAGCTGCTAACTGAGCCC; SEQ ID NO:12; F, 5'CCGAGAGCATACTCGGGAC; SEQ ID NO:13), respectively. PCR was carried out for 35 cycles of 30s at 94° C., 45s at 56° C. (*3) or 60° C. (*4), and 45s at 72° C. in 20 ul containing 20 ng of genomic DNA, 1.0 uM of each primer, 200 uM dNTPs, 10 mM Tris-HCl (pH 8.3), 1.5 mM MgCl$_2$, 50 mM KCl, and 0.5U AmpliTaq DNA polymerase (Hoffman-LaRoche).

CYP3A4 Polymorphism

The mutant allele (FIG. 3) CYP3A4*2 (A-290G) was detected by PCR amplification using the PCR primers 3A4F2 (5'TAGGTAAAGATCTGTAGGTGT3'; SEQ ID NO:14) and 3A4R1 (5'GCTTCTCCACCTTGGAAG3'; SEQ ID NO:15). PCR was carried out for 35 cycles of 30s at 94C., 30s at 56C. and 30s at 72C. in 25 ul containing 15 ng of genomic DNA, 0.25 uM of each primers, 100 um dNTPs, 10 mM Tris-HCl (pH 8.3), 1,5 mM MgCl$_2$, 50 mM KCl and 0.2U ampliTaq DNA polymerase (Hoffman-Laroche).

NAT2 Polymorphisms

A 1211 bp fragment containing the whole NAT2 coding region was amplified with primers P100 (5'GTCACACGAGGAAATCAAATGC3'; SEQ ID NO:1) and P56 (5'GTTTTCTAGCATGAATCACTCTGC3'; SEQ ID NO:3). PCR was carried out for 35 cycles of 30s at 94° C., 1 min at 62° C. and 2 min at 72° C. in 20 ul containing 20 ng of genomic DNA, 0.5 uM of each primer, 200 uM of each dNTPs, 10 mM Tris-HCl (pH 8.3), 50 mM KCl, 1.5 mM MgCl$_2$ and 1.0 U ampliTaq DNA polymerase (Hoffman-Laroche). In problematic cases, the same PCR product was used for two nested PCR. One was carried out with P100 (SEQ ID NO:1) and R1 (5'ACCCAGCATCGACAATGTAATTCCTGCCCTCA3'; SEQ ID NO:2), for 35 cycles of 30s at 94° C., 30s at 62° C. and 45s at 72° C. in 20 ul containing 1 ul of first-step PCR product, 0.5 uM of each primers, 200 uM of each dNTPs, 1.5 mM MgCl$_2$, 10 mM Tris-HCl (pH 8.3), 50 mM KCl, and 0.5U ampliTaq DNA polymerase (Hoffman-Laroche). In the second nested PCR was performed with 0.5 uM of primers P87 (5'CCTGGACCAAATCAGGAGAG3'; SEQ ID NO:4) and P90 (5'ACACAAGGGTTTATTTTGTTCC3'; SEQ ID NO:5). These mutations are then used to define six distinct alleles (FIG. 4), NAT2*4 (no mutation), NAT2*5A (presence of mutations at positions 341 and 481), NAT2*5B (presence of mutations at positions 341, 481 and 803), NAT2*5C (presence of mutations at positions 341 and 803), NAT*6A (presence of mutations at positions 282 and 590) and NAT*7B (presence of mutations at positions 282 and 857).

Dot-blots

Each PCR reaction was brought up to 100 μl with water, incubated at 94° C. for 2 min and cooled on ice; the solution was then made 10×SSC (1×SSC corresponds to 1.5 M NaCl, 150 mM sodium citrate, pH 7) by addition of 100 μl 20×SSC. Hundred μl aliquots were then applied in parallel onto a membrane filter to create two identical twin 48-dot blots. After rinsing with 100 μl of 10×SSC the membranes were immersed in 1.5 M NaCl, 0.5 M NaOH for 10 min and in 1.5 M NaCl, 0.5 M Tris HCl pH 7.2 for 15 min DNA was fixed by drying the membranes and exposing them to 254 nm UV at the energy of 120,000 μJ/cm$^2$ in Stratalinker 1800 (Stratagene).

ASO-hybridization

Pentadecanucleotides were synthesized complementary to each allelic variant identified, to serve as ASO-probes for DNA typing by dot-blot hybridization (Table 2).

Blots were pre-hybridized for 30 min (rotary oven) in 20 ml 1×SSPE (150 mM NaCl, 10 mM NaH$_2$PO, 1.1 mM EDTA, pH 7.4), 0.75 M NaCl, 70 mM Tris/HCl, pH 7.4 containing 1% SDS and 200 µg/ml heparin, at hybridization temperature, $T_H$ (see Table 2). ASO probes, 50 pmole, were 5'-labeled using γ-[$^{32}$P]-ATP (6,000 Ci/mmole) and T4 kinase (Gibco BRL) to a specific activity of 1–3×10$^6$ cpm/pmole (250,000–750,000 cpm/ng). Hybridization with the 0.8–2.0 pmole ASO probe (~2,000,000 cpm) was carried out for 40 min at $T_H$. Then the membranes were washed with 2×SSPE, 0.1% SDS for 10 min at room temperature, once or 2 times for 10 min at washing temperature (see Table 2) and exposed overnight at −80° C. with a screen. Identical twin membranes were probed by the allelic ASOs and always read in parallel. This compensated, if necessary, for varying concentrations of the individual amplified DNA samples and, by the same token, for the variance in the probe activity. In addition, DNA samples of known allelic content served as positive controls for the allelic probes. After stripping (5 min in boiling 0.5% SDS) the membranes were stored at room temperature (or at −20° C. for longer periods of time) and reused (up to 12 times) for hybridization with other probes.

Results and Discussion

To facilitate the analysis of mutations in the carcinogen metabolizing genes CYP1A1, CYP2D6, CYP3A4 and NAT2 (FIGS. 1–4) we have developed a PCR-ASO system for efficient screening of 11 mutations.

The numbering of nucleotide positions in FIG. 1 is as in Cascorbi et al. (1996b). Wild type, WT, and mutant variants are shown below where the effect of mutation on the integrity of the message or the protein coding (if any) is indicated. CYP1A11 represents WT; substitution T/C (position 6235) in 3' flanking region of the CYP1A1 gene defines CYP1A1*2A allele and in phase with the A/G base substitution at position 4889, causing substitution of Ile to Val (codon 462, it defines CYP1A1*2B allele; C/A substitution at position 4887, leading to replacement of Thr by Asp (codon 461), defines CYP1A1*4 allele.

Figure 2:
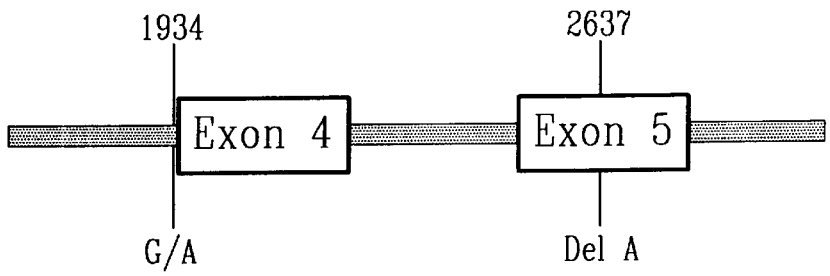
FIG. 2 illustrates mutations in the CYP2D6 locus.

The numbering of nucleotide positions in FIG. 2 is as in Sachse et al. (1997). Wild type, WT, and mutant variants are shown below where the effect of mutation on the integrity of the message or the protein coding (if any) is indicated. CYP2D6*1 is a wild type; CYP2D6*4 allele is defined by G/A mutation at site 1934 (last position of intron 3) which leads to an abnormal splicing, while a deletion at the position 2637 (CYP2D6*3) causes a frameshift at the Arg codon 259.

Figure 3:
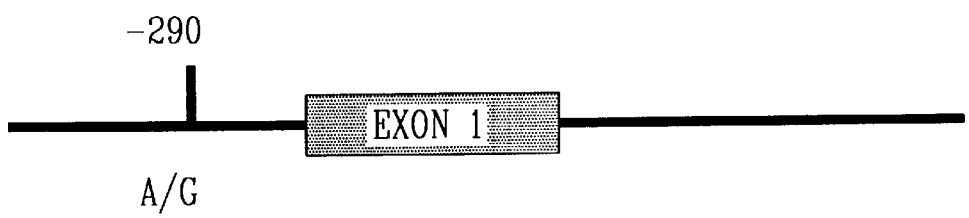
FIG. 3 illustrates mutation in the CYP3A4 locus.

The numbering of nucleotide positions in FIG. 3 is as in Hashimoto et al. (Hashimoto H et al., 1993, *Eur J Biochem.* 218:585–595). CYP3A4*1 is a wild type; CYP3A4*2 allele is defined by A/G mutation at site −290 in the 5' untranslated region.

Figure 4:
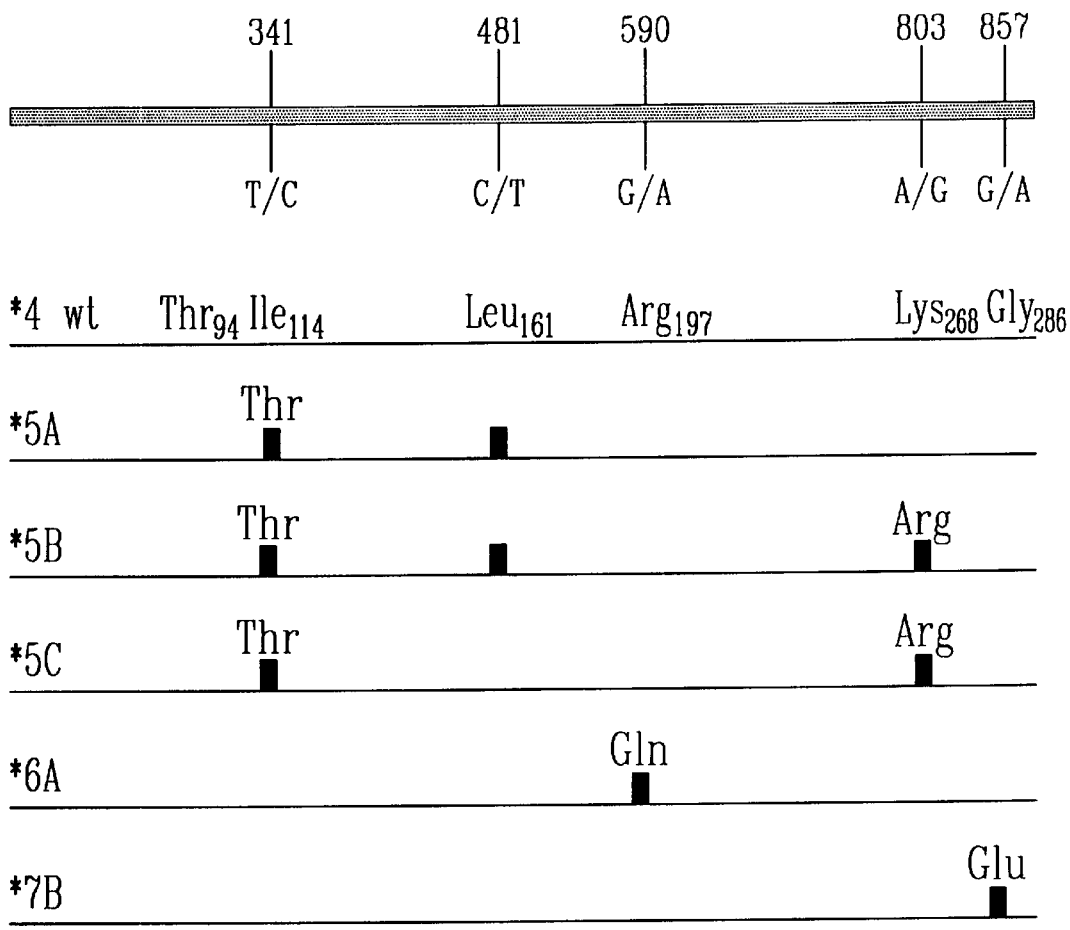
FIG. 4 illustrates mutations in the NAT2 locus.

The numbering of nucleotide positions in FIG. 4 is as in Cascorbi et al. (1996a). WT and mutant variants are shown below where the effect of mutation on the protein coding (if any) is indicated. NAT*5A allele is characterized by T/C substitution at position 341 causing Ile/Thr amino-acid replacement at codon 114 which is accompanied by silent C/T mutation at the position 481. An A/G base substitution at position 803 (Lys/Arg amino-acid substitution at codon 268) on NAT*5A background defines NAT2*5B allele. NAT2*5C differs from NAT2*5B by the absence of mutation at the 481 site. NAT2*6A allele is characterized by G/A substitution at the position 590 causing Arg/Gln replacement at codon 197. NAT2*7B allele is defined by G/A substitution at position 857 causing Gly/Glu replacement at codon 286. DNA fragments including sites of polymorphisms within CYP1A1, CYP2D6, CYP3A4 and NAT2 loci were amplified by PCR, dot-blotted and subsequently hybridized with ASOs. Representative hybridization blots are illustrated in FIG. 4.

Figure 5A:
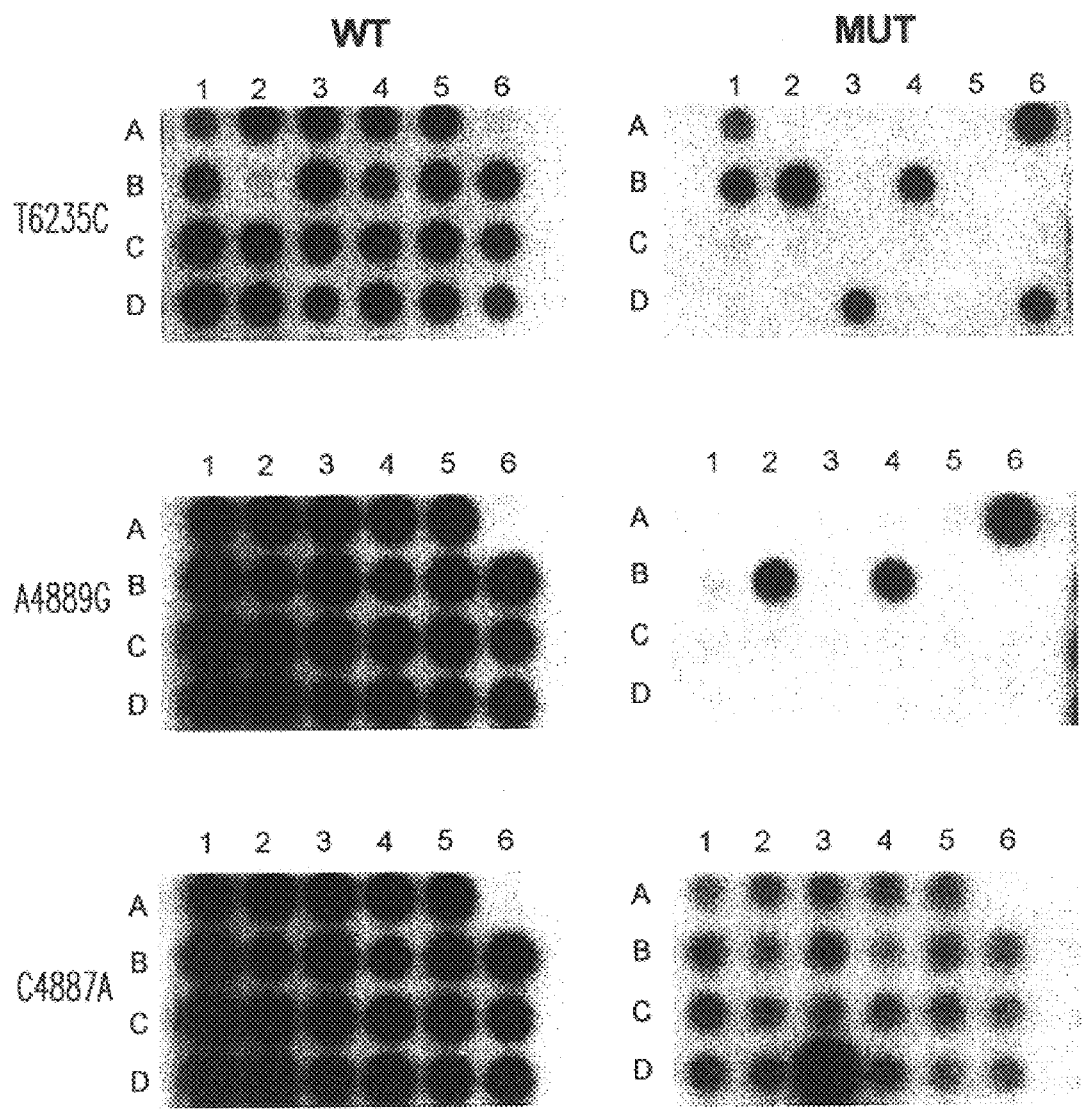
Figure 5B:
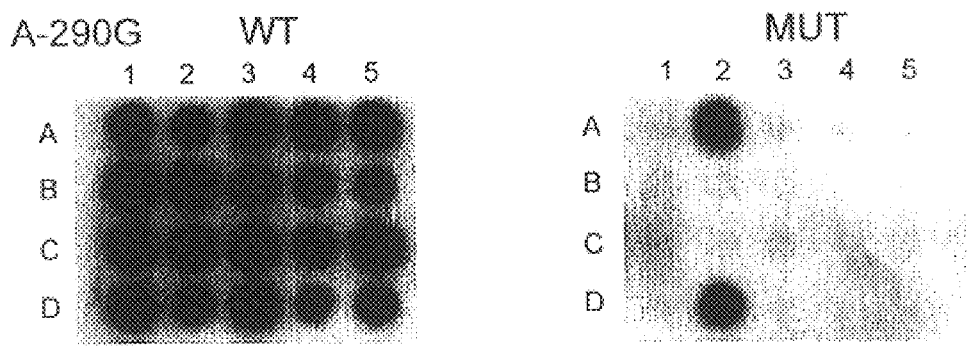
Figure 5B:
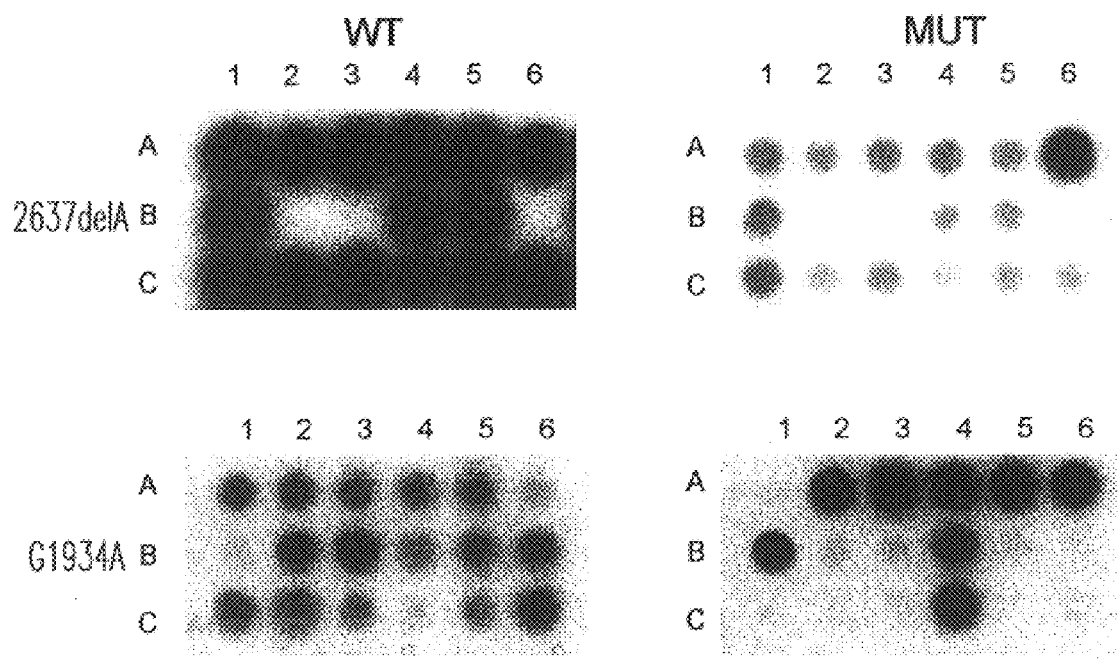

Positive hybridization signals with mutant probes indicate the presence of mutations, absence of the hybridization signal with the wild-type probe indicates mutant homozygous. A heterozygous individual will be illustrated by positive hybridization signals both with mutant and wild-type probes, whereas the absence of signal with the mutant ASO but a positive signal with the wild-type probe indicates a wild-type homozygous status (FIG. 5). Two 48-dots sister blots were probed with oligonucleotide-probes, specific for the wild type (left panels) or the mutant (right panels) alleles (FIG. 5). The name of the locus as well as the WT and MUT allele-specific oligonucleotide probes are indicated (only representative columns and rows from the twin blots are shown).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An isolated oligonucleotide molecule comprising a mutant allele of CYP1A1, which contains a point mutation at one position selected from the group consisting of position 4887, 4889, and 6235.

2. An isolated oligonucleotide molecule of claim 1, wherein said mutation is selected from the group consisting of an adenine at position 4887, a guanine at position 4889 and a cytosine at position 6235.

3. An isolated oligonucleotide molecule of claim 2, wherein said mutant oligonucleotide molecule has a nucleic acid sequence as set forth in SEQ ID NOS:27, 28 and 31.

4. An isolated oligonucleotide molecule comprising a wild-type allele of CYP1A1, wherein said normal nucleotide is selected from the group consisting of a cytosine at position 4887, a adenine at position 4889 and a thymine at position 6235.

5. An isolated oligonucleotide molecule as claimed in 4, wherein said wild type oligonucleotide molecule has a nucleic acid sequence as set forth in SEQ ID NOS:26, 29 and 30.

6. An isolated oligonucleotide molecule comprising a mutant allele of CYP3A4, contains a point mutation at position 290.

7. An isolated oligonucleotide molecule of claim 6, wherein said mutation is a guanine.

8. An isolated oligonucleotide molecule of claim 7, wherein said mutant oligonucleotide molecule has a nucleic acid sequence as set forth in SEQ ID NO:37.

9. An isolated oligonucleotide molecule comprising a mutant allele of CYP2D6, which contains a point mutation at one position selected from the group consisting of position 1934 and 2637.

10. An isolated oligonucleotide molecule of claim 9, wherein said mutation is selected from the group consisting of an adenine at position 1934 and a deletion at position 2637.

11. An isolated oligonucleotide molecule of claim 10, wherein said mutant oligonucleotide molecule has a nucleic acid sequence as set forth in SEQ ID NOS:33 and 35.

12. An isolated oligonucleotide molecule comprising a wild-type allele of CYP2D6, wherein said normal nucleotide is selected from the group consisting of a guanine at position 1934 and an adenine at position 2637.

13. An isolated oligonucleotide molecule as claimed in 12, wherein said wild type oligonucleotide molecule has a nucleic acid sequence as set forth in SEQ ID NOS:32 and 34.

14. An isolated oligonucleotide molecule comprising a mutant allele of NAT2, which contains a point mutation at one position selected from the group consisting of position 341, 481, 590, 803, and 857.

15. An isolated oligonucleotide molecule of claim 14, wherein said mutation is selected from the group consisting of a cytosine at position 341, a thymine at position 481, an adenine at position 590, a guanine at position 803, and an adenine at position 857.

16. An isolated oligonucleotide molecule of claim 15, wherein said mutant oligonucleotide molecule has a nucleic acid sequence as set forth in SEQ ID NOS:16, 18, 20, 23, and 24.

17. An isolated oligonucleotide molecule comprising a wild-type allele of NAT2, wherein said normal nucleotide is selected from the group consisting of a thymine at position 341, a cytosine at position 481, a guanine at position 590, an adenine at position 803, and a guanine at position 857.

18. An isolated oligonucleotide molecule as claimed in 17, wherein said wild type oligonucleotide molecule has a nucleic acid sequence as set forth in SEQ ID NOS:17, 19, 21, 22, and 25.

* * * * *